(12) United States Patent
Talin et al.

(10) Patent No.: US 9,428,525 B1
(45) Date of Patent: Aug. 30, 2016

(54) TUNABLE ELECTRICAL CONDUCTIVITY IN METAL-ORGANIC FRAMEWORK THIN FILM DEVICES

(71) Applicant: Sandia Corporation, Albuquerque, NM (US)

(72) Inventors: Albert Alec Talin, Dublin, CA (US); Mark D. Allendorf, Pleasanton, CA (US); Vitalie Stavila, Pleasanton, CA (US); Francois Leonard, Brentwood, CA (US)

(73) Assignee: Sandia Corporation, Albuquerque, NM (US)

( * ) Notice: Subject to any disclaimer, the term of this patent is extended or adjusted under 35 U.S.C. 154(b) by 0 days.

(21) Appl. No.: 15/132,038

(22) Filed: Apr. 18, 2016

Related U.S. Application Data

(62) Division of application No. 14/469,459, filed on Aug. 26, 2014, now Pat. No. 9,346,831.

(51) Int. Cl.
*C07F 1/08* (2006.01)

(52) U.S. Cl.
CPC ................................. *C07F 1/08* (2013.01)

(58) Field of Classification Search
CPC ...... B01J 20/223; B01J 20/226; B01J 31/16; B01J 31/1691; C07F 1/08
See application file for complete search history.

(56) References Cited

U.S. PATENT DOCUMENTS 9,346,831 B1 *   5/2016   Talin .................. B01J 20/226

* cited by examiner

*Primary Examiner* — Sudhakar Katakam
(74) *Attorney, Agent, or Firm* — Madelynne J. Farber

(57) ABSTRACT

A composition including a porous metal organic framework (MOF) including an open metal site and a guest species capable of charge transfer that can coordinate with the open metal site, wherein the composition is electrically conductive. A method including infiltrating a porous metal organic framework (MOF) including an open metal site with a guest species that is capable of charge transfer; and coordinating the guest species to the open metal site to form a composition including an electrical conductivity greater than an electrical conductivity of the MOF.

10 Claims, 10 Drawing Sheets

TUNABLE ELECTRICAL CONDUCTIVITY IN METAL-ORGANIC FRAMEWORK THIN FILM DEVICES

CROSS-REFERENCE TO RELATED APPLICATION

This application is a divisional application of, and discloses subject matter that is related to subject matter disclosed in, co-pending parent application U.S. Ser. No. 14/469,459, filed Aug. 26, 2014 and entitled "TUNABLE ELECTRICAL CONDUCTIVITY IN METAL-ORGANIC FRAMEWORK THIN FILM DEVICES" which claimed the benefit of U.S. Provisional Patent Application No. 61/870, 839, filed Aug. 28, 2013 entitled "TUNABLE ELECTRICAL CONDUCTIVITY IN METAL-ORGANIC FRAMEWORK THIN FILM DEVICES". The present application claims the priority of its parent application which is hereby incorporated by reference, in its entirety, for all purposes.

STATEMENT OF GOVERNMENT RIGHTS

This invention was developed under Contract DE-AC04-94AL85000 between Sandia Corporation and the U.S. Department of Energy. The U.S. Government has certain rights in this invention.

FIELD

Metal-organic frameworks and organic semiconductor devices and uses.

BACKGROUND

Metal-organic frameworks (MOFs) are crystalline materials with a nanoporous supramolecular structure consisting of metal ions connected by organic ligands. Their tailorable porosity, ease of synthesis, and ultra-high surface areas, combined with a broad choice of suitable building blocks make them promising materials for gas storage, chemical separation, catalysis, chemical sensing, and drug delivery. Unfortunately, MOFs are usually poor electrical conductors because of the insulating character of the organic ligands and the poor overlap between their π orbitals and the d orbitals of the metal ions. Combining the crystalline order of MOFs with an ability to conduct electrical charge has the potential to create a new class of materials that would open a suite of unique applications. While strategies to engineer electrically conducting MOFs have been proposed (e.g., using second- or third-row transition metals, redox-active linkers, and heterobimetallic structures), few of these approaches have been realized. Until recently only one example of an intrinsically conducting framework with permanent porosity was known: a p-type semiconducting MOF in which conductivity occurs via a redox mechanism. Very recently, Gandara et al. described a series of metal triazolate MOFs, one of which exhibits Ohmic conductivity. Although the mechanism of conductivity in that case is not known, it appears to be highly specific to the presence of divalent iron in the structure, as MOFs in this series with the same structure but different divalent metals are not conducting. To date there is no report of a conducting MOF thin film device.

SUMMARY

In one embodiment, a composition including a porous metal organic framework (MOF) including an open metal site and a guest species capable of charge transfer that can coordinate with the open metal site, wherein the composition is electrically conductive is described. In another embodiment, a method including infiltrating a porous metal organic framework (MOF) including an open metal site with a guest species that is capable of charge transfer; and coordinating the guest species to the open metal site to form a composition including an electrical conductivity greater than an electrical conductivity of the MOF is described.

DETAILED DESCRIPTION

In one embodiment, a composition is disclosed. The composition includes a porous MOF and a guest species that participates in charge transfer with the MOF. By combining a MOF and a guest species that participates in charge transfer with the MOF, the composition is electrically conductive. In another embodiment, a thin film device is disclosed. The device includes a thin film of a MOF infiltrated with a guest species that participates in charge transfer with the MOF. In another embodiment, the electrical transport properties of a MOF thin film device are tunable while preserving the MOF structure.

In one embodiment, a MOF is a compound including metal ions or clusters coordinated to organic ligands. Suitable metal ions or clusters include copper ions (e.g., $Cu^{2+}$), and ions of chromium (Cr), iron (Fe), nickel (Ni), molybdenum (Mo) and ruthenium (Ru). In one embodiment, a suitable MOF includes $Cu_3(BTC)_2$ also known as HKUST-1.

In one embodiment, a guest species that participates in charge transfer with the MOF includes a delocalized $\pi$ electron or $\pi$ electrons. Representative guest species include one or more nitrile moieties, one or more thiol moieties, one or more carbonyl moieties, one or more thiolate moieties, one or more amine moieties, one or more imine moieties, one or more hydroxyl moieties, or a mixture thereof. A moiety is used generally to identify a portion of a molecule. In one embodiment, the guest species is 7,7,8,8-tetracyanoquinododimethane (TCNQ), a molecule having multiple nitrile moieties. In one embodiment, a composition includes a porous MOF of $Cu_3(BTC)_2$ and a guest species of TCNQ. Without wishing to be bound by theory, it is believed the recited moieties of respective molecules participate in the charge transfer with the MOF and thus, are responsible for imparting electrical conductivity to the composition (MOF and guest species). In another embodiment, a representative guest species is a molecule that has a configuration that will interact with a MOF to impart electrical conductivity. Representative molecules include thiophenes, dithiophenes, tetrathiafulvalene, imidazole, triazole, tetrazole and derivatives and/or mixtures thereof. In a further embodiment, a representative guest species is a transition metal complex operable to undergo an outer sphere electron transfer. Examples include, but are not limited to, ruthenium hexamine, hexacyanoferrate and hexacyanocobaltrate. Such complexes can be assembled into bulk semiconducting coordination polymers operable to undergo a charge transfer reaction with an MOF resulting in conducting behavior.

Figure 1A:
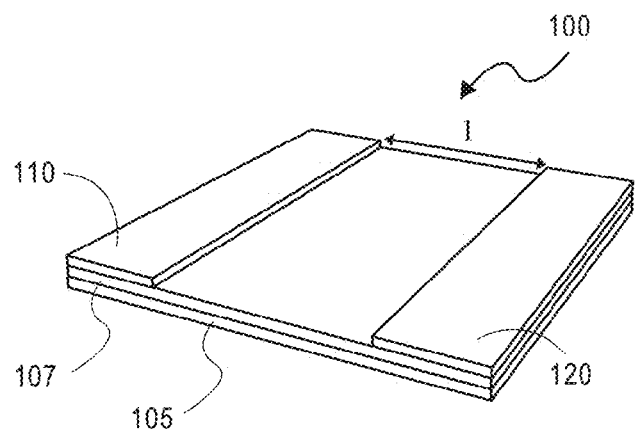
FIG. 1A shows a top perspective view of a portion of a substrate including components of a thin film device including conductive pads.
Figure 1B:
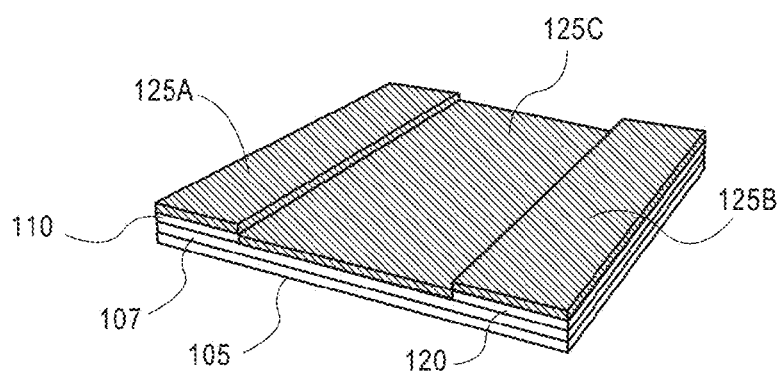
FIG. 1B shows structure of FIG. 1A following the introduction of a porous MOF onto the conductive pads and the insulating layer therebetween.
Figure 1C:
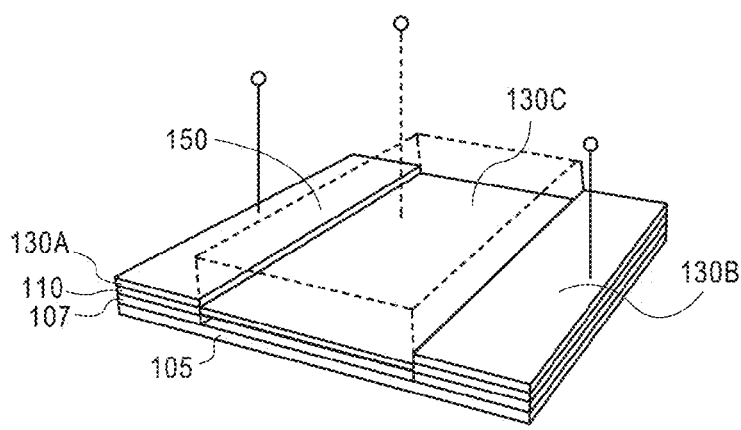
FIG. 1C shows the structure of FIG. 1B following the infiltration of the $Cu_3(BTC)_2$ MOF with a guest species of 7,7,8,8-tetracyanoquinododimethane (TCNQ) and the formation of a gate electrode on the device and contacts to MOF films and the gate electrode of the thin film device.

FIGS. 1A-1C illustrate a method of forming an electrically conductive MOF thin film devices on a substrate. Referring to FIG. 1A, structure 100 includes substrate 105 that is, for example, a portion of a silicon wafer. In one embodiment, substrate 105 includes a device layer including a number of devices (e.g., transistor devices) and circuits (CMOS) established through metallization to the devices. Overlying a surface of substrate 105 (a top surface as viewed) is dielectric layer 107 of, for example, silicon dioxide that is grown on the substrate. In one embodiment, dielectric layer 107 has a thickness on the order of 100 nanometers (nm). As shown in FIG. 1A, also disposed on substrate 105 and on dielectric layer 107 are two conductive pads separated by a channel length, l. Representative lengths for channel length, l, include 100 microns (μm), 150 μm and 200 μm. In one embodiment, conductive pad 110 and conductive pad 120, respectively, are each a metal material such as platinum (Pt). Representative dimensions of each of conductive pads 110 and 120 are 800 μm by 400 μm. A representative thickness of conductive pads 110 and 120 is 100 nm.

Figure 2A:
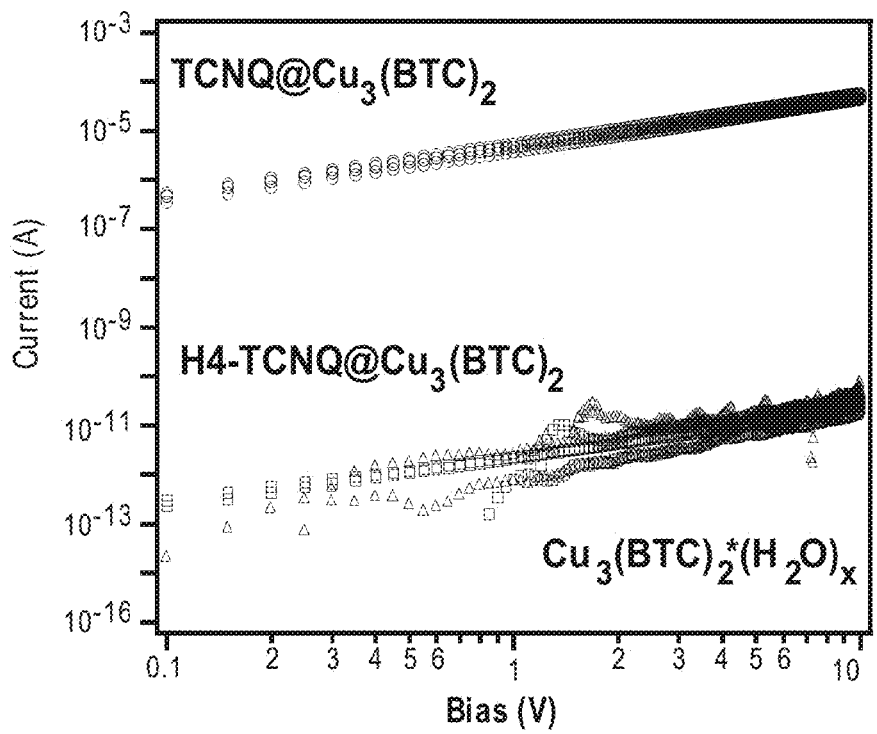
FIG. 2A shows current-voltage graphs of a thin film MOF of $Cu_3(BTC)_2$ and a TCNQ infiltrated MOF thin film and a hydrated infiltrated MOF.

FIG. 1B shows structure 100 of FIG. 1A following the introduction of a porous MOF onto conductive pad 110 and conductive pad 120, as well as over the dielectric layer 107. In one embodiment, porous MOF is a film of $Cu_3(BTC)_2$ conformally introduced on a surface of structure 100 including conductive pad 110, conductive pad 120, and dielectric layer 107. A representative nominal thickness of a film of a porous MOF is 100 nm. Representatively, a $Cu_3(BTC)_2$ film may be grown on dielectric layer 107 in a liquid cell reactor as described in the art. In one embodiment, a polycrystalline $Cu_3(BTC)_2 \cdot xH_2O$ film was grown with preferred orientation along the (111) direction. FIG. 1B shows MOF film portion 125A and MOF film portion 125B on conductive pad 110 and conductive pad 120, respectively, and MOF film portion 125C in a channel region or area of the structure. Current voltage (I-V) characteristics obtained for an as-grown thin film device in ambient are shown in FIG. 2A. A very small conductivity ($\sim 10^{-6}$ S/m) is observed, consistent with the expected insulating nature of $Cu_3(BTC)_2$.

Figure 2B:
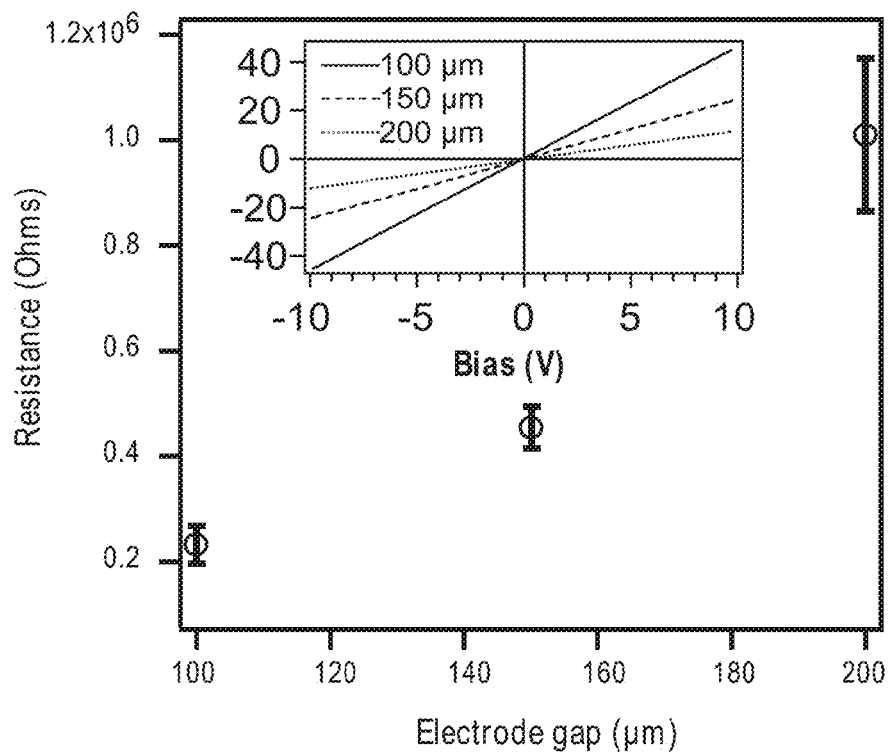
FIG. 2B shows a graph of electrical resistance versus channel length for the thin film device of FIG. 1C.
Figure 2C:
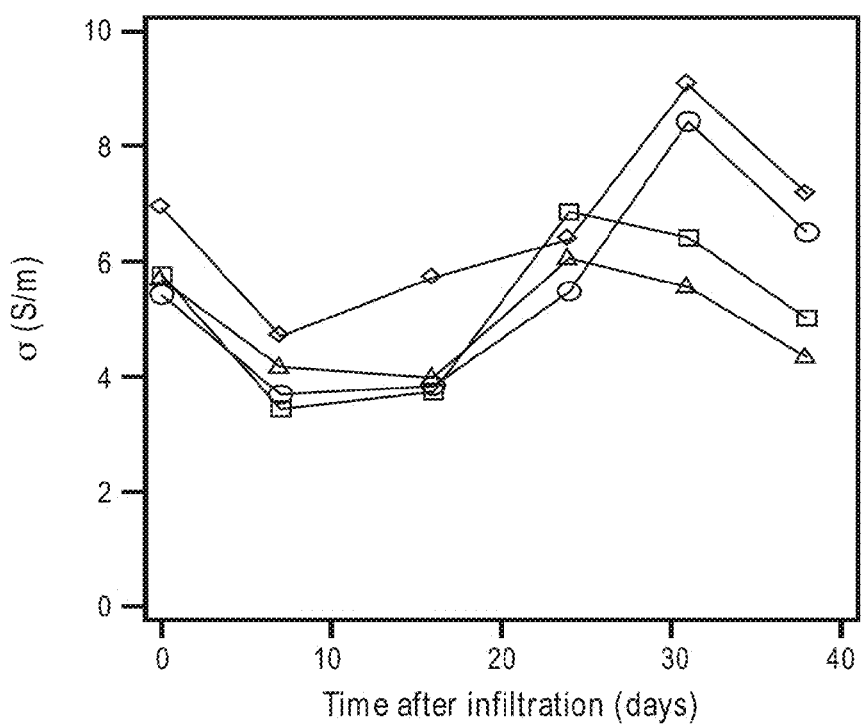
FIG. 2C shows a graph of a conductivity of a TCNQ-MOF thin film of FIG. 1C over time.
Figure 2D:
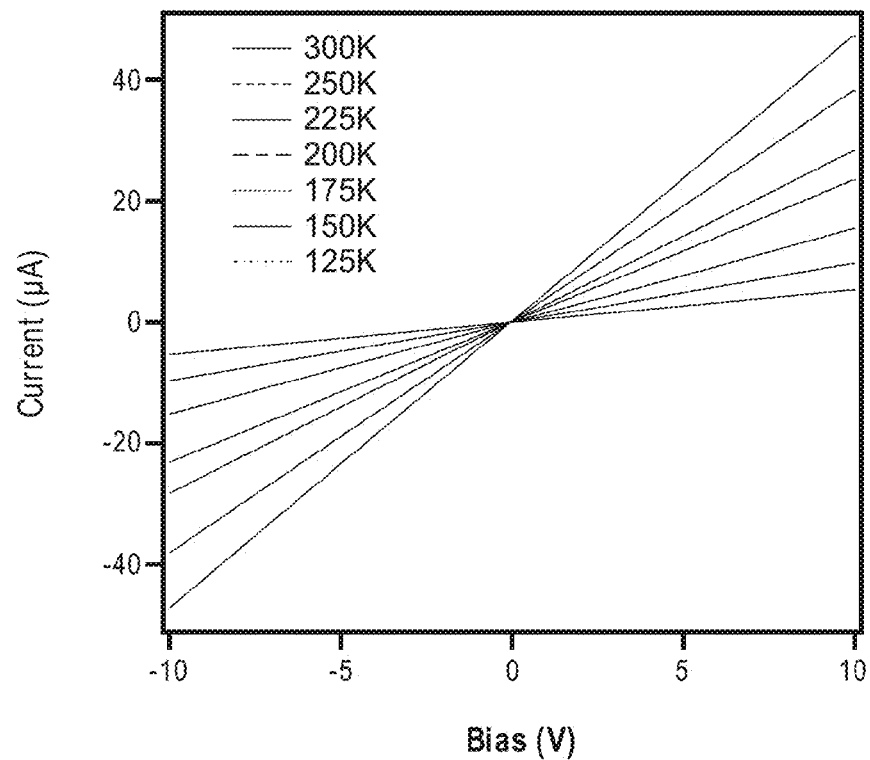
FIG. 2D shows a graph of a thin film TCNQ infiltrated MOF at different temperatures.
Figure 2E:
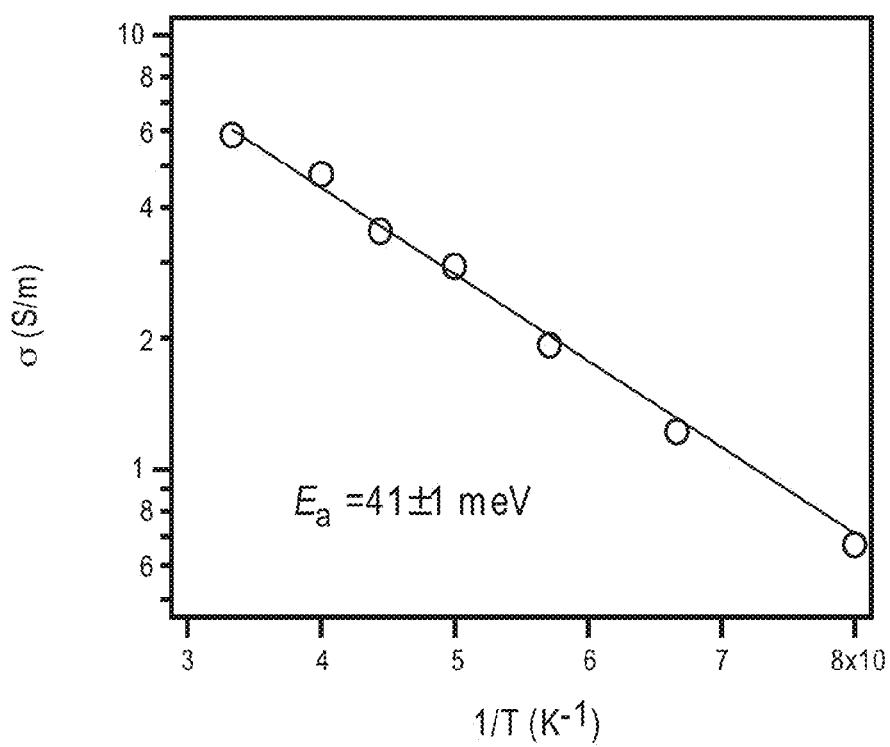
FIG. 2E shows a graph of conductivity as a function of temperature of a thin film TCNQ infiltrated MOF.

FIG. 1C shows the structure of FIG. 1B following the infiltration of the $Cu_3(BTC)_2$ MOF in areas corresponding to 125A, 125B, and 125C with a guest species. In one embodiment, the MOF films were infiltrated with a guest species of 7,7,8,8-tetracyanoquinododimethane (TCNQ) by heating in vacuum at 180° C. for 30 minutes to remove the water molecules, and then immediately transferring to a saturated $TCNQ/CH_2Cl_2$ solution for infiltration. FIG. 1C shows film 130A on conductive pad 110, film 130B on conductive pad 120, and film 130C in a channel region each illustrative of an infiltrated MOF. I-V curves for four such devices after 72 hours of exposure to the TCNQ solution are shown in FIG. 2A. The infiltration leads to dramatic increase of the current, with a linear I-V curve with conductivity of 7 S/m, six orders of magnitude larger than the un-infiltrated devices. Measurements as a function of channel length (FIG. 2B) show a monotonic increase of resistance with increasing electrode separation (increasing l) thus indicating that contact resistance effects are not at the origin of the phenomenon. Further, the TCNQ-infiltrated devices are stable in ambient over a long period of time (FIG. 2C). The temperature dependence of the conductivity was also measured. The conductivity decreases with decreasing temperature (FIG. 2D-2E) and follows a thermally activated relation $\sigma \sim \exp(-E_a/T)$ with a low activation energy $E_a$ of 41±1 meV, similar to values reported for high mobility organic polymeric semiconductors such as poly-3-hexylthiophene (P3HT).

In one embodiment, as shown in FIG. 1C, a thin film device can also include an electrical gate structure to which a voltage is applied, which can be disposed on film 130C either oriented above or below film 130C. FIG. 1C shows an embodiment where gate structure is oriented above film 130C as viewed (gate structure 150 shown in dashed lines). If the gate structure is oriented above film 130C, an additional insulating layer may be present between the gate structure and film 130C. The gate electrode serves to modulate the electrical current in the MOF device.

The above results show large conductance increases of a porous MOF through guest specie infiltration. It has also been found that the conductivity can be tuned. One technique for tuning the conductivity of a porous MOF involves modifying an exposure time of the MOF to the guest species.

Figure 2F:
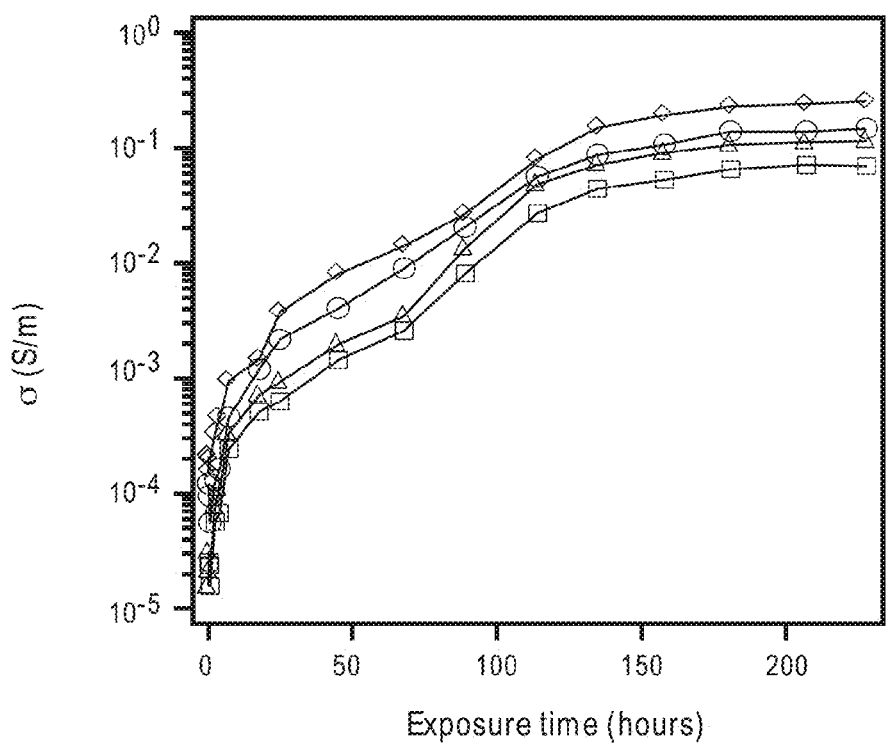
FIG. 2F shows a graph of conductivity as a function of exposure time for a TCNQ guest species.

As shown for several devices in FIG. 2F, the conductivity can be controlled over several orders of magnitude by changing the exposure time. Furthermore, the time scale over which the conductivity varies is relatively long, implying that accurate control over the conductivity can be achieved.

EXAMPLE 1

Figure 3:
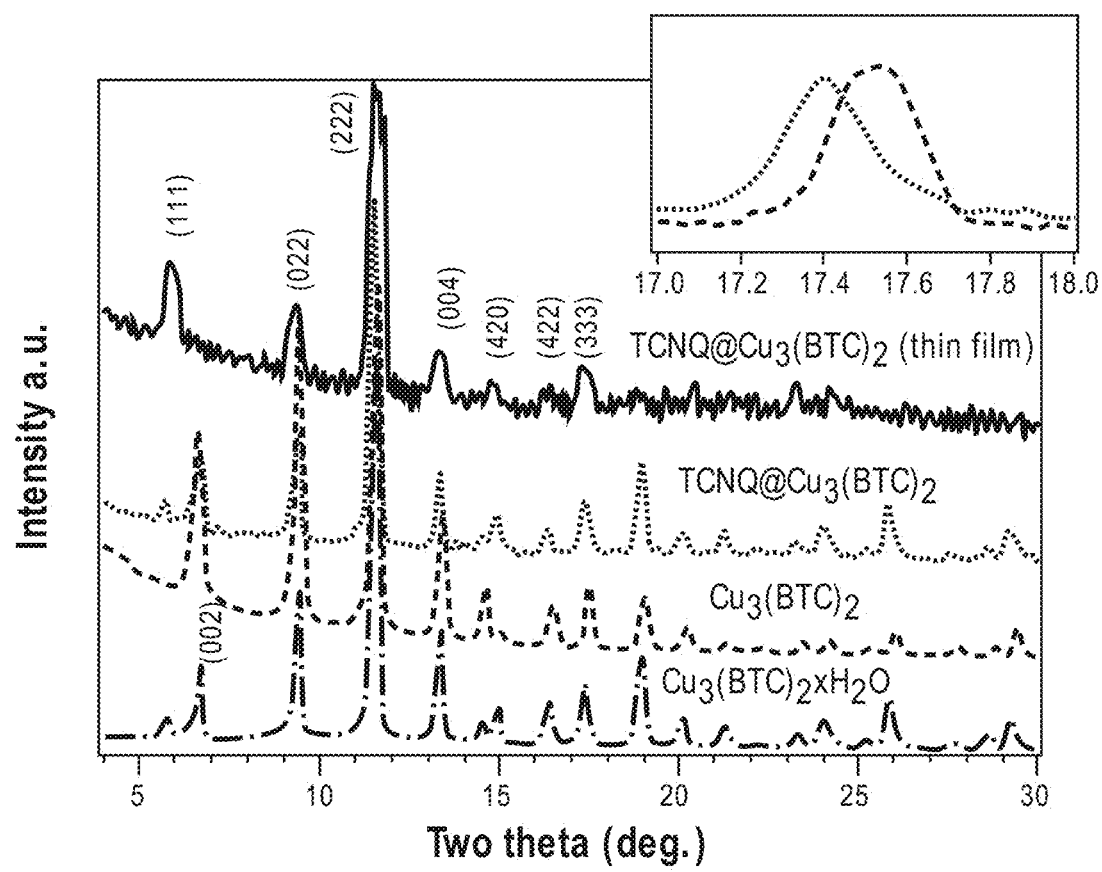
FIG. 3 shows x-ray diffraction data for $Cu_3(BTC)_2$ powder and thin film and each infiltrated with TCNQ.

A number of experiments to verify the TCNQ infiltration of a MOF were conducted. Powder XRD patterns of as-synthesized $Cu_3(BTC)_2 \cdot xH_2O$, $Cu_3(BTC)_2$ (activated) and $Cu_3(BTC)_2$ (infiltrated) with TCNQ (hereinafter TCNQ@$Cu_3(BTC)_2$) show that the MOF crystalline structure (face centered cubic, $Fm\bar{3}m$) is unaffected by the infiltration process. The inset in FIG. 3D shows that the MOF lattice expands slightly upon TCNQ adsorption; Rietveld refinement yielded lattice parameters of 2.617 nm±0.001 nm and 2.635 nm±0.001 nm, for $Cu_3(BTC)_2$ and TCNQ@$Cu_3(BTC)_2$ powders, respectively. In addition, the surface area of the activated $Cu_3(BTC)_2$ powder, obtained from $N_2$ adsorption isotherms using the Brunauer, Emmett, and Teller (BET) method is 1844 $m^2$ $g^{-1}$±4 $m^2g^{-1}$. This value is typical of high-quality $Cu_3(BTC)_2$ material with little or no pore collapse or residual reactant. After drying in air, the TCNQ@$Cu_3(BTC)_2$ material displays a BET surface area of 214 $m^2$ $g^{-1}$±0.5 $m^2$ $g^{-1}$ suggesting high TCNQ loading. This result is confirmed by elemental analysis indicating a $Cu_3(BTC)_2$: TCNQ ratio of two based on carbon, nitrogen, and hydrogen content, corresponding to about eight TCNQ molecules per unit cell or one TCNQ molecule per MOF pore. Furthermore, visual examination of the powdered MOFs reveals an expected turquoise-blue color for the as-synthesized material and the violet-blue hue for the activated (dehydrated) MOF. Upon exposure to TCNQ, the color of the crystals changes to teal, clearly indicating a perturbation of the MOF. The color of TCNQ@$Cu_3(BTC)_2$ does not change upon exposure to air indicating that TCNQ is not displaced by atmosphere water vapor. In contrast, the color of the activated MOF prior to TCNQ infiltration reverts almost instantly to that of the as-synthesized (hydrated) material when exposed to atmospheric moisture.

Figure 4A:
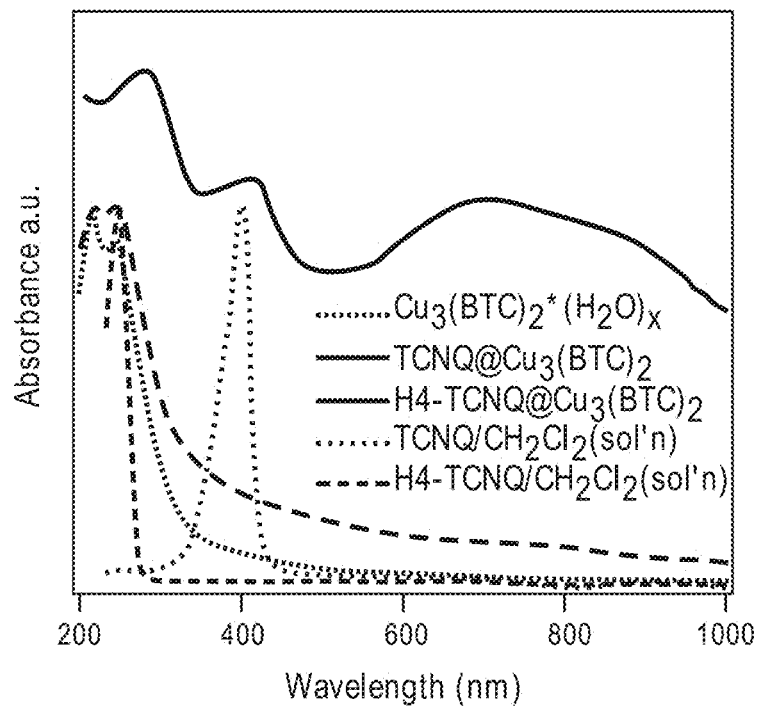
FIG. 4A shows an absorption spectrum of films of a MOF of $Cu_3(BTC)_2$, a MOF of $Cu_3(BTC)_2$ infiltrated with TCNQ and a hydrated infiltrated MOF as well as TCNQ in $CH_2CH_2$ and hydrated TCNQ in $CH_2CH_2$.
Figure 4B:
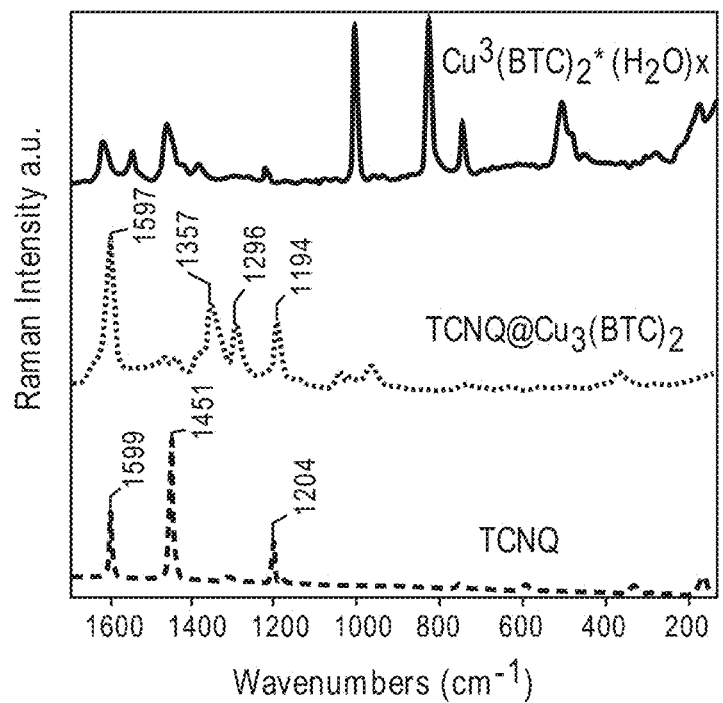
FIG. 4B shows Raman spectra of a MOF of $Cu_3(BTC)_2$, a MOF of $Cu_3(BTC)_2$ infiltrated with TCNQ and TCNQ.

The TCNQ/MOF interaction was probed in several ways. UV-Vis spectra were collected on films of the uninfiltrated $Cu_3(BTC)_2 \cdot (H_2O)_x$, several ways. TCNQ@$Cu_3(BTC)_2$, H4-TCNQ@$Cu_3(BTC)_2$, as well as solutions of TCNQ and H4-TCNQ. The UV-visible absorption spectrum of a TCNQ@$Cu_3(BTC)_2$ film (FIG. 4A) shows expected MOF peak at 340 nm, a peak at 410 nm associated with neutral TCNQ, as well as a broad absorption bands centered at ~690 nm and ~850 nm that is absent in both $Cu_3(BTC)_2 \cdot (H_2O)_x$ and TCNQ in $CH_2Cl_2$. These additional bands are characteristic of TCNQ radical indicating charge transfer between the framework and TCNQ. In addition, Raman spectra of TCNQ@$Cu_3(BTC)_2$ (FIG. 4B) are dominated by TCNQ peaks with frequencies shifted from those of neat TCNQ. The TCNQ C=C stretching frequency shifts from 1451 $cm^{-1}$ to 1357 $cm^{-1}$ and a new peak at 1296 $cm^{-1}$ appears a strong indication that TCNQ interacts with the available coordination sites on the $Cu^{2+}$ ions in the framework.

Figure 4C:
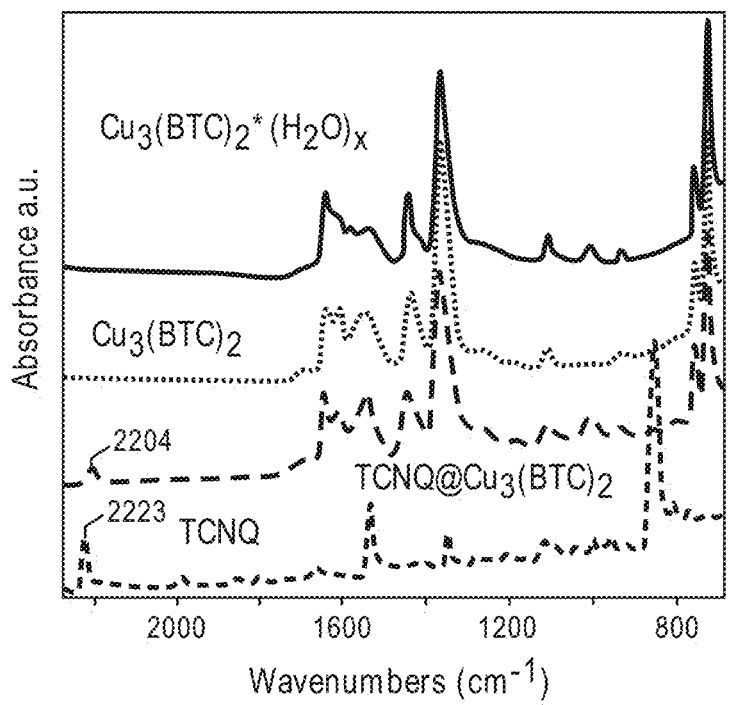
FIG. 4C shows infrared absorption spectra of a MOF of $Cu_3(BTC)_2.xH_2O$, $Cu_3(BTC)_2$, $TCNQ@Cu_3(BTC)_2$ and TCNQ powder.
Figure 4D:
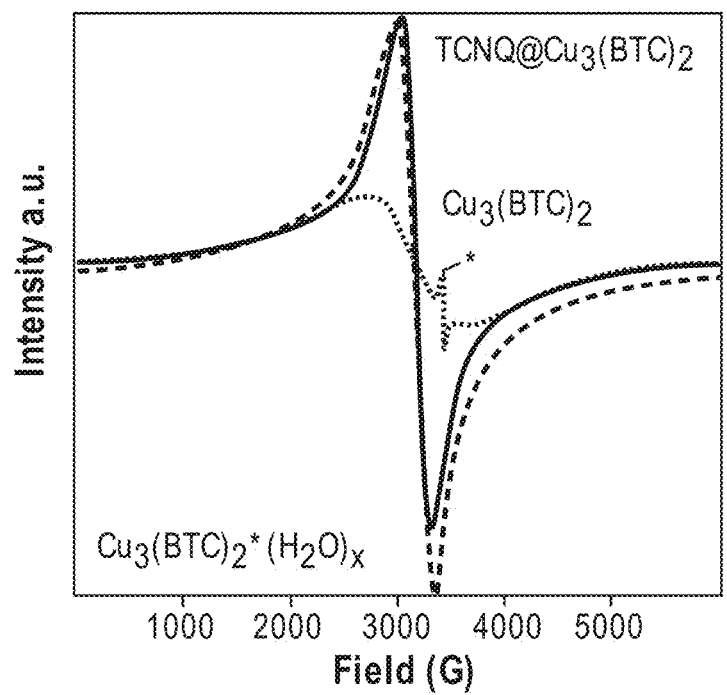
FIG. 4D shows room temperature continuous wave electron paramagnetic resonance spectra of activated $Cu_3(BTC)_2$, $Cu_3(BTC)_2$ stirred in methanol, and $Cu_3(BTC)_2$ stirred in methanol containing TCNQ (the asterisk (*) denotes an unidentified organic radical signal observed only in the activated $Cu_3(BTC)_2$ sample.

The infrared absorption peaks of $Cu_3(BTC)_2$ are also affected by infiltration with TCNQ (FIG. 4C). Peaks at 2223 $cm^{-1}$ (C≡N stretching) and 1541 $cm^{-1}$ (C=C stretching) shift to 2204 $cm^{-1}$ and 1508 $cm^-$, respectively. The frequency of the C≡N stretching is widely used to characterize the degree of charge transfer (z) in molecular TCNQ charge transfer complexes according to $z=(v_0-v)/44$ $cm^-$ where $v_0$ is the frequency of neutral TCNQ (≈2223 $cm^{-1}$) and v is the frequency observed in the molecular complex (2204 $cm^{-1}$ for TCNQ@$Cu_3(BTC)_2$). According to this interpretation, the extent of charge transfer estimated for TCNQ@$Cu_3(BTC)_2$ is 0.43 electron charges. This is further supported by room temperature electron paramagnetic resonance spectroscopy of TCNQ@$Cu_3(BTC)_2$ (FIG. 4D) that exhibit no evidence of isolated TCNQ radical anion, consistent with partial charge-transfer between Cu and TCNQ.

To test the importance of the guest/host interactions, experiments were carried out where TCNQ was replaced with its fully hydrogenated counterpart, H4-TCNQ (cyclohexane-1,4-diylidene)dimalononitrile), which lacks a delocalized π electron network. Elemental analysis indicates that the loading is similar to that of TCNQ, i.e., about one H4-TCNQ molecule per pore. The corresponding I-V curve (FIG. 2A) is essentially the same as the uninfiltrated MOF. This result suggests that the availability of guest molecule orbitals that can accept charge, as is the case in TCNQ but no H4-TCNQ, is crucial for achieving high conductivity.

Figure 4E:
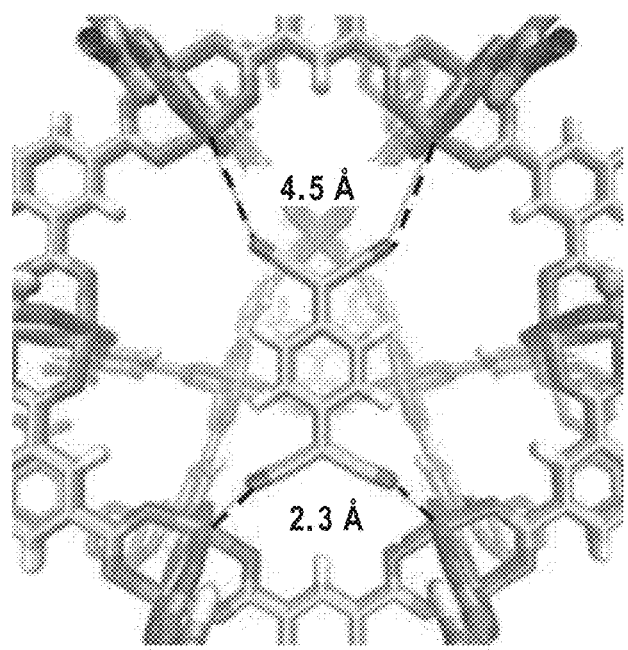
FIG. 4E shows a representation of a minimum energy configuration for $TCNQ@Cu_3(BTC)_2$ obtained from ab initio calculations.
Figure 4F:
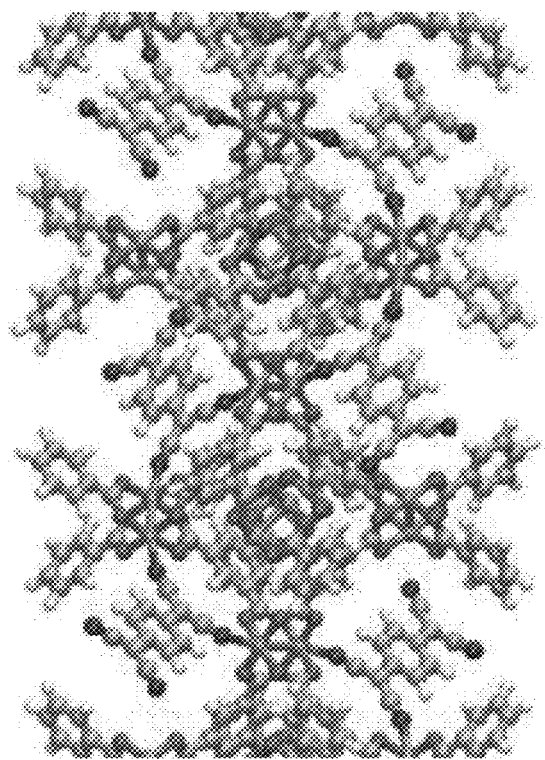
FIG. 4F shows an illustration of a possible configuration for $TCNQ@Cu_3(BTC)_2$ that would provide a conductive channel through the MOF unit cell.

Ab initio calculations of the TCNQ@$Cu_3(BTC)_2$ hybrids were performed. As illustrated in FIG. 4E, favorable binding of the TCNQ (binding energy of 53.7 kJ/mol) was found when it bridges two nearby copper paddlewheels. This configuration suggests a possible mechanism for the appearance of conductance in this material: a path through a MOF unit cell can be created by using four TCNQ molecules to bridge copper sites (FIG. 4F).

This synthetic approach is generalizable to other MOFs and other guest molecules. For example, it is anticipated that MOFs containing paddlewheel-type structures, such as the NOTT, rht and nbo MOFs as well as MOF-74 (including the extended versions) and other MOFs containing open metal sites, will exhibit conducting behaviors. Examples of other guest molecules include thiols, thiophenes, diimides, molecules with conjugated pi systems, selenium and tellurium compounds and nitric oxides.

In conclusion, the incorporation of guest molecules into MOFs can lead to a sharp and tunable increase in the electrical conductivity while preserving the MOF porous, crystalline structure. The results suggest a novel strategy for creating families of electrically conducting MOFs, providing highly ordered, supramolecular electronic materials with applications including conformal electronic devices, reconfigurable electronics, sensors (e.g., electrochemical sensors, chemiresistors, piezoresistors, impedance sensors, and field-effect transistors), displays, low-cost electronics (logic, memory, etc.) and energy conversion and storage devices (such as photovoltaics, batteries, capacitors).

EXAMPLE 2

Figure 5A:
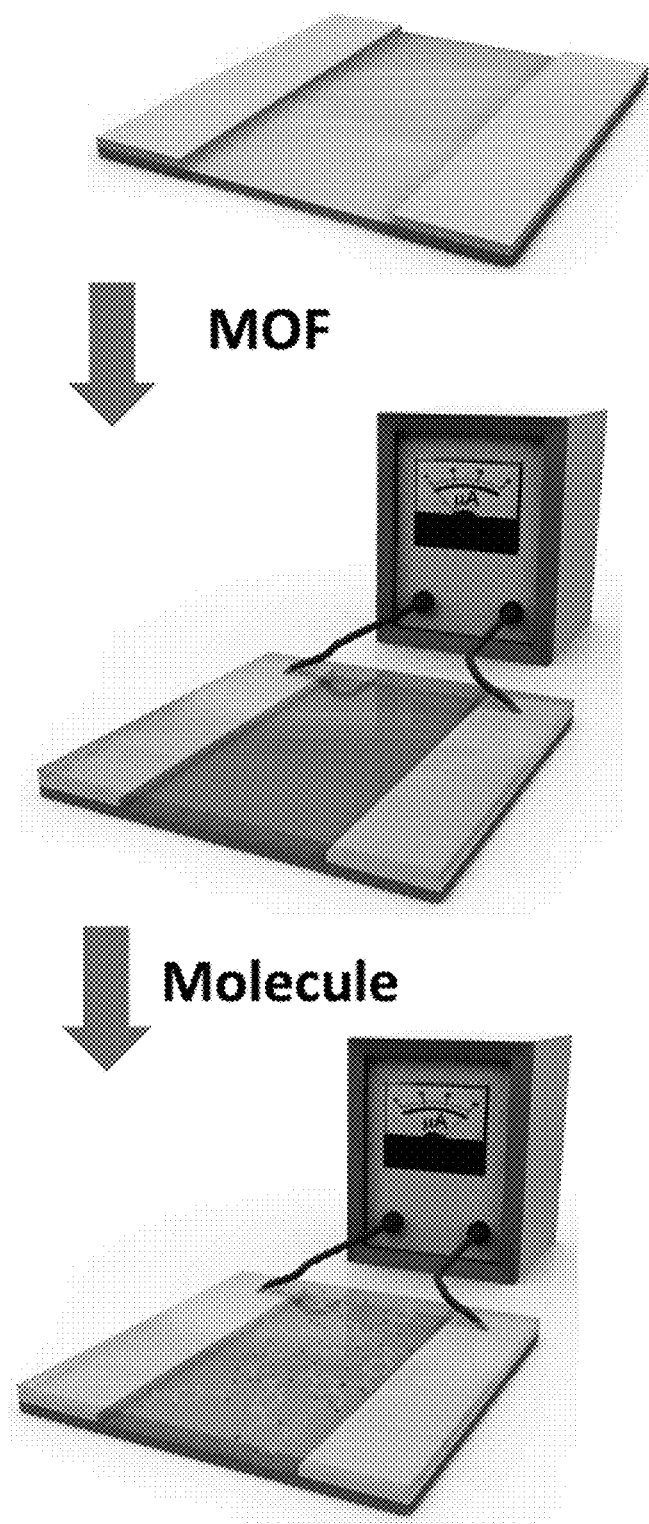
FIGS. 5A, 5B and 5C show a process for fabrication of conductive metal-organic framework thin film devices, and structural characterization data. (5A) A thin film of metal-organic framework is grown on an insulating wafer pre-patterned with electrodes. Molecules are then infiltrated by exposing the thin film device to a solution containing the molecules. (5B) A TCNQ molecule shown above a $Cu_3(BTC)_2$ MOF with arrow pointing to the pore. (5C) SEM image of MOF thin film device with optical images of devices before and after TCNQ infiltration.
Figure 5B:
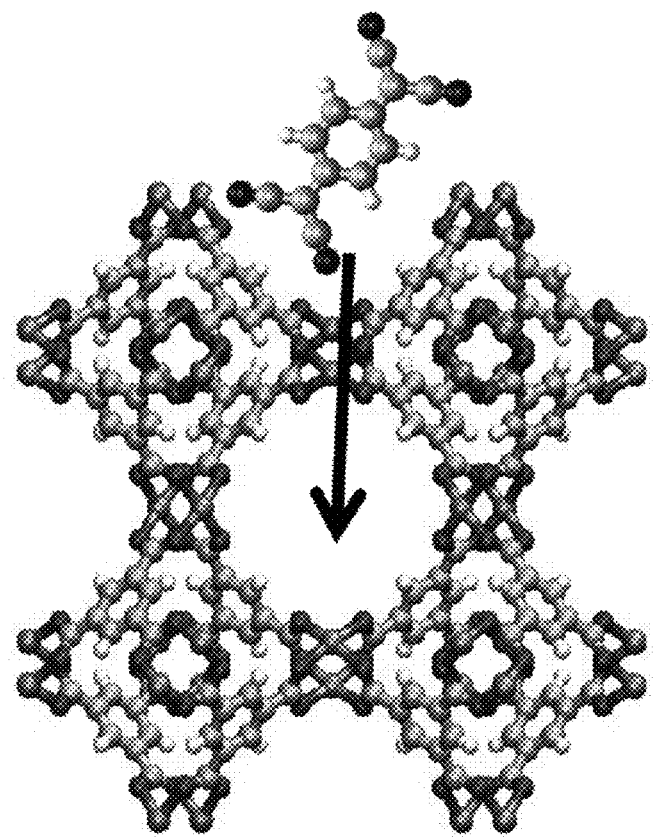
Figure 5C:
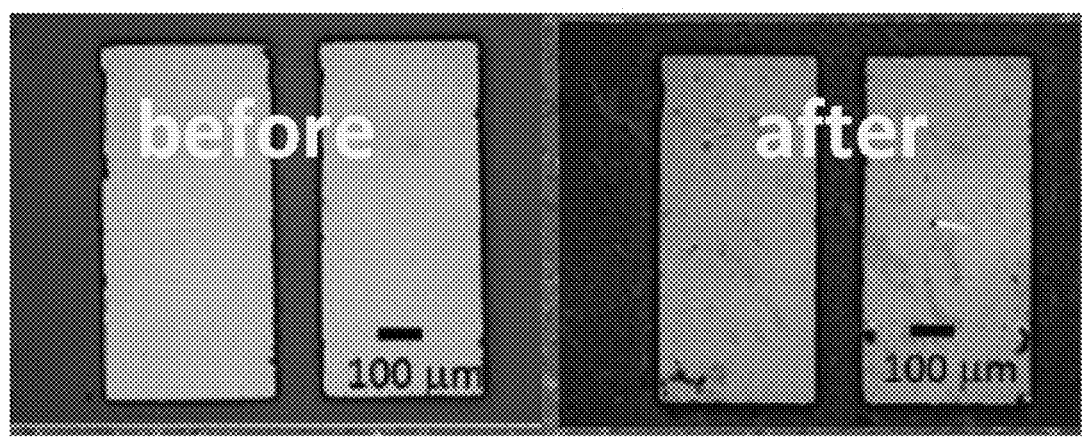

Our approach for realizing conductive MOF thin film devices is shown in FIGS. 5A and 5B. Si wafers with 100 nm of $SiO_2$ were pre-patterned with 100 nm-thick Pt pads (dimensions of 800 μm by 400 μm) and gaps of 100 μm, 150 μm, and 200 μm. $Cu_3(BTC)_2$ films with 100 nm nominal thickness were grown on the wafers in a liquid cell reactor as described previously. Grazing incidence SEM imaging (FIG. 5C) and XRD measurements (FIG. 3) indicate that a polycrystalline $Cu_3(BTC)_2 \cdot xH_2O$ film was grown with preferred orientation along the (111) direction.

In the description above, for the purposes of explanation, numerous specific details have been set forth in order to provide a thorough understanding of the embodiments. It will be apparent however, to one skilled in the art, that one or more other embodiments may be practiced without some of these specific details. The particular embodiments described are not provided to limit the invention but to illustrate it. The scope of the invention is not to be determined by the specific examples provided above but only by the claims below. In other instances, well-known structures, devices, and operations have been shown in block diagram form or without detail in order to avoid obscuring the understanding of the description. Where considered appropriate, reference numerals or terminal portions of reference numerals have been repeated among the figures to indicate corresponding or analogous elements, which may optionally have similar characteristics.

It should also be appreciated that reference throughout this specification to "one embodiment", "an embodiment", "one or more embodiments", or "different embodiments", for example, means that a particular feature may be included in the practice of the invention. Similarly, it should be appreciated that in the description various features are sometimes grouped together in a single embodiment, figure, or description thereof for the purpose of streamlining the disclosure and aiding in the understanding of various inventive aspects. This method of disclosure, however, is not to be interpreted as reflecting an intention that the invention requires more features than are expressly recited in each claim. Rather, as the following claims reflect, inventive aspects may lie in less than all features of a single disclosed embodiment. Thus, the claims following the Detailed Description are hereby expressly incorporated into this Detailed Description, with each claim standing on its own as a separate embodiment of the invention.

What is claimed is:

1. A method comprising:
   infiltrating a porous metal organic framework (MOF) comprising an open metal site, wherein the MOF comprises a plurality of metal ions or metal clusters and a plurality of organic ligands, with a guest species that is capable of charge transfer, wherein the guest species is located within a pore of the MOF; and
   coordinating the guest species to the open metal site to form a composition comprising an electrical conductivity greater than an electrical conductivity of the MOF.

2. The method of claim 1, wherein infiltrating comprises exposing the MOF to the guest species for a period of time.

3. The method of claim 2, wherein an electrical conductivity of the composition is related to the exposure time.

4. The method of claim 1, wherein the MOF comprises copper.

5. The method of claim 4, wherein the MOF comprises $Cu_3(BTC)_2$.

6. The method of claim 4, wherein the guest species comprises a nitrile moiety, a thiol moiety, or a carbonyl moiety.

7. The method of claim 4, wherein the guest species comprises 7,7,8,8-tetracyanoquinododimethane.

8. The method of claim 5, wherein the guest species comprises 7,7,8,8-tetracyanoquinododimethane.

9. The method of claim 1, wherein the guest species is selected from the group consisting of a nitrile moiety, a thiol moiety, a carbonyl moiety, a thiolate moiety, an amine moiety, an imine moiety, a hydroxyl moiety, or a mixture thereof.

10. The method of claim 1, wherein the guest species is selected from the group consisting of a thiophene, a dithiopene, a tetrathiafulvalene, an imidazole, a triazole, a tetrazole, or a derivative thereof or a transition metal complex operable to undergo an outer sphere electron transfer.

* * * * *